US 008815788 B2

(12) United States Patent
Osborn et al.

(10) Patent No.: US 8,815,788 B2
(45) Date of Patent: Aug. 26, 2014

(54) AEROSOL DEODORIZER

(75) Inventors: Morey E. Osborn, Cedar Park, TX (US); Babak R. Samani, Cedar Park, TX (US)

(73) Assignee: HighQ Services, LLC, Cedar Park, TX (US)

(*) Notice: Subject to any disclaimer, the term of this patent is extended or adjusted under 35 U.S.C. 154(b) by 546 days.

(21) Appl. No.: 13/005,533

(22) Filed: Jan. 12, 2011

(65) Prior Publication Data

US 2011/0177992 A1 Jul. 21, 2011

Related U.S. Application Data

(60) Provisional application No. 61/296,356, filed on Jan. 19, 2010, provisional application No. 61/380,455, filed on Sep. 7, 2010.

(51) Int. Cl.
*C11D 3/48* (2006.01)
*C11D 3/00* (2006.01)
C11D 3/50 (2006.01)
C11D 3/43 (2006.01)

(52) U.S. Cl.
CPC ............... *C11D 3/0068* (2013.01); C11D 3/50 (2013.01); *C11D 3/48* (2013.01); C11D 3/43 (2013.01)
USPC .......................................................... 510/191

(58) Field of Classification Search
CPC .......... C11D 3/0068; C11D 3/50; C11D 3/48; C11D 3/43
USPC .......................................................... 510/191
See application file for complete search history.

(56) References Cited

U.S. PATENT DOCUMENTS

| | | | | |
|---|---|---|---|---|
| 5,880,076 | A * | 3/1999 | Vermeer | 510/123 |
| 6,753,305 | B2 * | 6/2004 | Raso et al. | 510/438 |
| 7,148,187 | B1 * | 12/2006 | Simon et al. | 510/235 |
| 7,446,082 | B2 * | 11/2008 | Kilkenny et al. | 510/191 |
| 7,446,084 | B2 * | 11/2008 | Barthel et al. | 510/296 |
| 7,470,652 | B2 * | 12/2008 | Kilkenny et al. | 510/191 |
| 7,491,686 | B2 * | 2/2009 | Barthel et al. | 510/446 |
| 2003/0096722 | A1 * | 5/2003 | Caselli et al. | 510/382 |
| 2005/0155628 | A1 * | 7/2005 | Kilkenny et al. | 134/6 |
| 2005/0155630 | A1 * | 7/2005 | Kilkenny et al. | 134/6 |
| 2006/0128585 | A1 * | 6/2006 | Adair et al. | 510/383 |
| 2006/0293201 | A1 * | 12/2006 | Simon et al. | 510/235 |
| 2006/0293202 | A1 * | 12/2006 | Cate et al. | 510/235 |
| 2008/0045434 | A1 * | 2/2008 | Barthel et al. | 510/439 |
| 2008/0207481 | A1 * | 8/2008 | Meine et al. | 512/4 |
| 2008/0221003 | A1 * | 9/2008 | Meine et al. | 510/103 |
| 2009/0081755 | A1 * | 3/2009 | Schmiedel et al. | 435/183 |
| 2009/0165228 | A1 * | 7/2009 | Kilkenny et al. | 15/104.94 |
| 2010/0140368 | A1 * | 6/2010 | de Lame et al. | 239/1 |
| 2010/0184855 | A1 * | 7/2010 | Bernhardt et al. | 514/529 |

* cited by examiner

*Primary Examiner* — Gregory Webb

(57) ABSTRACT

A cleaning solution includes an aqueous base, 0.1 wt % to 10 wt % of an organic acid, 0.1 wt % to 35 wt % of a surfactant, 0.1 wt % to 10 wt % of an organic ester derived from a carboxylic acid having at least 4 carbons, and 0.1 wt % to 11 wt % of an ethylene glycol ether.

20 Claims, 2 Drawing Sheets

AEROSOL DEODORIZER

CROSS-REFERENCE TO RELATED APPLICATION(S)

The present application claims priority from U.S. Provisional Patent Application No. 61/296,356, filed Jan. 19, 2010, entitled "BACTERIA COLONY GROWTH INHIBITOR IN EASILY APPLIED FORM," naming inventor Morey E. Osborn, which application is incorporated by reference herein in its entirety.

The present application claims priority from U.S. Provisional Patent Application No. 61/380,455, filed Sep. 7, 2010, entitled "NANODEX—A DISPENSING DEVICE CONTAINING A MATERIAL CAPABLE OF COMBATING NITROGENOUS MALODORS BY ADDITION ELIMINATION REACTION, SALT FORMATION AND SOLVENT-INDUCED MIGRATION," naming inventors Morey E. Osborn and Babak R. Samani, which application is incorporated by reference herein in its entirety.

FIELD OF THE DISCLOSURE

This disclosure, in general, relates to solutions having deodorizing properties and, in particular, solutions having deodorizing properties that can be applied as an aerosol.

BACKGROUND

From the dawn of the modern age many people have at one time or another contemplated ways to cope with or eliminate malodorous air or infectious contamination. A number of methods have been employed, including burning candles, use of incense, opening windows, use of fans, spraying fragrances or other masking agents, or any combination thereof. Such methods are generally ineffective and a nuisance to implement.

Odors urea particular annoyance and in closed small spaces. For example, people are increasingly spending time in cars, tracking contaminants in and out of cars, and eating in cars. In addition, air leaks from outside the car and can introduce malodors into the enclosed space within a car. Such malodors can accumulate within the car, making travel within the vehicle unpleasant.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

Figure 1:
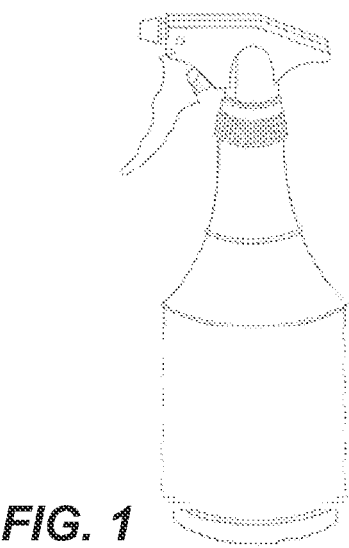
FIG. 1 includes an illustration of an exemplary spray bottle.

In an embodiment, a deodorizing solution includes a nano-sized titanium dioxide particulate and a polymer dispersed in an aqueous solution. In an example, the polymer is water-miscible and forms a coating upon drying. In another example, the polymer is in the form of an emulsion. The solution can also include an alcohol, such as an ethyl alcohol or an isopropyl alcohol. In an example, the deodorizing solution can be applied in aerosol form.

In another embodiment, a cleaning solution includes an aqueous base, an organic acid, a surfactant, an organic ester, and an ethylene glycol ether. Optionally, the solution can include a fragrance. In another example, the solution can include a dispersed polymer. In particular, the organic ester is derived from a carboxylic acid having at least four carbons. The surfactant can be a nonionic surfactant or an anionic surfactant. An exemplary organic acid includes citric acid. The solution can be applied in aerosol form.

In a first embodiment, a deodorizing solution can include an aqueous base, titanium dioxide, an alcohol, and a polymer. As described in detail below, the aqueous solution can be sprayed or aerosolized and applied to a surface. Alternatively, the deodorizing solution can be applied with a cloth, sponge, or rag. Once applied to a surface, the deodorizing solution forms a deodorizing coating.

In an example, the deodorizing solution includes titanium dioxide particulate, such as microcrystalline titanium dioxide particulate. The titanium dioxide particulate can have an average particle size of 1 nanometer to 10000 nanometer, such as not greater than 100 nanometers. For example, the titanium dioxide particulate can have a particle size of not greater than 60 nanometers, such as not greater than 50 nanometers. Further, the titanium dioxide particulate can have an average particle size of at least 3 nanometers, such as at least 10 nanometers, or at least 30 nanometers. The solution can include the titanium dioxide particulate in an amount of 0.1 wt %-30 wt % based on the weight of the deodorizing solution, such as an amount of 0.1 wt % to 6 wt %, an amount of 1 wt % to 6 wt %, an amount of 2 wt % to 6 wt %, or an amount of 3 wt % to 6 wt %.

In addition, the deodorizing solution can include an alcohol, such as a low molecular weight alcohol. For example, the alcohol can include an alcohol having between 2 and 6 carbons, such as between 2 and 4 carbons. In an example, the alcohol is ethanol. In another example, the alcohol is isopropyl alcohol. The alcohol can be present in the solution in an amount of 0.5 wt % to 20 wt % based on the total weight of the deodorizing solution, such as an amount of 0.5 wt % to 5 wt %, an amount of 0.5 wt % to 3 wt %, or amount of 0.5 wt % to 2 wt % based on the total weight of the deodorizing solution.

Further, the deodorizing solution includes a polymer. The polymer can be water-miscible polymer or can be emulsified within the aqueous base. In particular, when the deodorizing solution is applied to a surface and the water evaporates, the polymer can dry or cure, forming a coating on the surface. In an example, the polymer is included in an amount of 1 wt % to 20 wt % based on the total weight of the deodorizing solution, such as an amount of 3 wt % to 15 wt %, 5 wt % to 15 wt %, 7 wt % to 15 wt %, or even 8 wt % to 15 wt % based on the total weight of the deodorizing solution.

An exemplary polymer includes polyethylene glycol, polypropylene glycol, polyvinyl chloride, polyvinyl acetate, partially-hydrolyzed polyvinyl acetate, ethylene vinyl acetate copolymer, polyvinyl alcohol, polyester such as polyethylene terephthalate (PET), polycarbonate, polyacrylate, acrylic esters, polyacrylonitrile, hydrolyzed polyacrylonitrile, polyolefin such as polyethylene, polypropylene, or blends or copolymers thereof, polyamide such as Nylon, polysiloxanes, polyurethane, a product of polyethylene diamine and adipic acid, fluoropolymer, or blends or copolymers thereof, or any combination thereof. For example, the polymer can be an acrylic polymer. In another example, the polymer is polyvinyl acetate. In a further example, the polymer is a silicone polymer. In another example, the polymer is polyurethane. In an additional example, the polymer is a polyamide. In a further example, the polymer is a polyvinyl chloride. In an additional example, the polymer is poly alkyl glycol, such as polyethylene glycol or polypropylene glycol. Further, the polymer can be a polyolefin, such as polyethylene or polypropylene. An exemplary fluoropolymer can be formed of a homopolymer, copolymer, terpolymer or polymer blend formed from a monomer, such as tetrafluoroethylene, hexafluoropropylene, chlorotrifluoroethylene, trifluoroethylene, vinylidene fluoride, vinyl fluoride, perfluoropropyl vinyl ether, perfluoromethyl vinyl ether, or any combination thereof. An exemplary fluoropolymer includes polytetrafluoroethylene (PTFE), a fluorinated ethylene propylene copolymer (FEP), a copolymer of tetrafluoroethylene and perfluoropropyl vinyl ether (perfluoroalkoxy or PFA), a copolymer of tetrafluoroethylene and perfluoromethyl vinyl ether (MFA), a copolymer of ethylene and tetrafluoroethylene (ETFE), a copolymer of ethylene and chlorotrifluoroethylene (ECTFE), polychlorotrifluoroethylene (PCTFE), poly vinylidene fluoride (PVDF), a terpolymer including tetrafluoroethylene, hexafluoropropylene, and vinylidenefluoride (THV), or any blend or any alloy thereof. In particular, the polymer dries or cures to form a UV transparent coating.

Optionally, the deodorizing solution can include an emulsifier or surfactant, for example, in an amount of 0.3 wt % to 9 wt %, such as an amount of 2 wt % to 8 wt %. The surfactant can be a nonionic surfactant, an anionic surfactant, a polymeric surfactant, a cationic surfactant, or any combination thereof. In a particular example, the surfactant includes a nonionic surfactant, such as an ethoxylate based surfactant.

The deodorizing solution can also include quaternary ammonium salts. An exemplary quaternary ammonium salts includes benzalkonium chloride. The quaternary ammonium salt can be included in amount of not greater than 5 wt %, not greater than 4 wt %, or even not greater than 3 wt % based on the total weight of the deodorizing solution.

The deodorizing solution can have a near neutral pH. For example, the pH of the deodorizing solution can be in a range of 6 to 9, such as a range of 6.8 to 8, or even a range of 6.8 to 7.5.

The deodorizing solution is particularly beneficial for eliminating odors associated with bacterial growth. While the deodorizing solution can additionally include fragrances or colorants, the deodorizing solution can consist essentially of an aqueous solution, a water-miscible or emulsified polymer, the titanium dioxide particulate, and optionally a surfactant, which provide advantages associated with reducing malodors caused by bacteria particularly when the coating formed by such a solution is exposed to ultraviolet radiation. As such, the deodorizing solution is particularly well adapted for use in automobiles and other surfaces exposed to UV or sunlight.

In another embodiment, a cleaning solution includes an aqueous base, an organic acid, a surfactant, an organic ester, and ethylene glycol ether. Optionally, the cleaning solution can include a fragrance. In another example, the cleaning solution can include a polymer. Such a cleaning solution can also be used in spray or aerosol form and can be applied to surfaces.

In an example, the cleaning solution includes an organic acid in an amount of 0.1 wt % to 10 wt % based on the total weight of the cleaning solution. For example, the organic acid can be included in the solution in an amount of 0.1 wt % to 8 wt %, such as an amount of 0.5 wt % to 7 wt % or an amount of 4 wt % to 7 wt % based on the total weight of the cleaning solution. In an alternative example, the organic acid can be included in the solution in an amount of 0.5 wt % to 3 wt % based on the total weight of the cleaning solution. An exemplary organic acid includes ascorbic acid, aspartic acid, citric acid, maleic acid, oxalic acid, succinic acid, glycolic acid, lactic acid, mane acid, tartaric acid, glutaric acid, mandelic acid, malonic acid, adipic acid, phthalic acid, or any combination thereof. In particular, the organic acid can be an alpha hydroxy carboxylic acid, such as a glycolic acid, lactic acid, citric acid, mandelic acid, maleic acid, tartaric acid, or any combination thereof. In particular example, the organic acid includes citric acid.

The cleaning solution can also include an organic ester in an amount of 0.1 wt % to 10 wt % based on the total weight of the cleaning solution. For example, the organic ester can be included in an amount of 0.1 wt % to 8 wt %, such as an amount of 0.1 wt % to 3.5 wt %, an amount of 0.4 wt % to 3 wt %, or an amount of 0.7 wt % to 2 wt % based on the total weight of the cleaning solution. In particular, the organic ester is a facile organic ester derived from a carboxylic acid having at least 4 carbons. For example, the carboxylic acid can include 4 to 16 carbons, such as 4 to 10 carbons, or 4 to 8 carbons. Further, the organic ester can be a methyl, ethyl, propyl, or butyl ester of the carboxylic acid. In particular, the organic ester can be a methyl or ethyl ester of the carboxylic acid.

An exemplary organic ester includes methyl or ethyl butyrate, methyl or ethyl salicylate, methyl or ethyl valerate, methyl or ethyl amylate, ethyl or methyl hexanoate esters, or any combination thereof. Such organic esters can also be mixed with propanoate or acetate organic esters. In a particular example, the organic ester is an aliphatic organic ester, such as a butyrate or hexanoate organic ester. In particular, the organic ester can be a butyrate organic ester. In another example, the organic ester is an aromatic organic ester, such as a salicylate organic ester.

In addition to the organic ester or alternatively, the cleaning solution can include an aldehyde, such as an alkyl-aldehyde, a cyclic aldehyde, an aromatic aldehyde, a heterocyclic aldehyde, or any combination thereof. An alkyl-aldehyde is alkane or alkene having an aldehyde functional group. An exemplary alkyl-aldehyde includes decanal, undecanal, dodecanal, undecene-10-al, 2-methyl-undecanal, 2,6,10-trimethyl-9-undecene-al, 2,3,5,5-tetramethyl-hexanal, or any combination thereof. An exemplary cyclic aldehyde includes 1-formyl-2,4-dimethyl$_7$ 2-cyclohexene and 1-formyl-3,5-dimethyl-4-cyclohexene, 1-formyl-2,3,5-trimethyl-4-cyclohexene and 1-formyl-2,4,6-trimethyl-3-cyclohexene, ([5.2.1.0$^{0.6}$]-tricyclo-8-decylidene)-4-butanal, 2,6,10-trimethyl-9-undecene-al, (4-methyl-3-pentene-yl)-4-cyclohexene-3-ylcarboxaldehyde, 7-formyl-5-isopropyl-2-methyl-2,2,2-bicyclo-2-octene, 2-formyl-8-dimethyl-1,2,3,4,5,6,7,8-octahydro-naphthalene, or any combination thereof. An aromatic aldehyde includes benzyl or other unsaturated cyclic carbon compounds including an aldhyde functional group. An exemplary aromatic aldehyde includes benzaldehyde, anisic aldehyde, heliotropine, veratric aldehyde, vanillin, isovanillin, ethylvanillin, cinnamaldehyde, cilantro, retinal, or any combination thereof. In a particular example, the aromatic aldehyde is a phenolic aldehyde, such as vanillin, isovanillin, ethylvanillin, cinnamaldehyde, cilantro, retinal, or any combination thereof. In an example, a heterocyclic aldehyde includes at least one heterocyclic ring and an aldehyde functional group. For example, a heterocyclic aldehyde includes pyridoxal. Other exemplary aldehydes include terpenic aldehydes, such as citronellal 3,7-dimethyl-6-octen-1-al or campholenic aldehyde; aliphatic aldehydes substituted by an aromatic group, such as α-methyl-3,4-methylene-dioxyhydrocinnamic aldehyde, cyclamen aldehyde, lilial, canthoxal$^R$, phenylacetic aldehyde, 3-phenyl-propionic aldehyde, or hydratropic aldehyde; aldehydes possessing another function such as the ether-oxide or alcohol functions, such as alkoxy-acetaldehydes, w-hydroxy aldehydes (e.g., hydroxy-citronellal), or w-alkoxy-aldehydes; aldehydes which possess a non-aromatic type unsaturation carried by the carbon in the alpha position of the aldehyde function, such as citral (neral and geranial), myrtenal, perilla aldehyde, or variously substituted 2-furyl carboxaldehydes; aldehydes which possess an ethylene unsaturation in alpha position, itself conjugated with an aromatic ring, such as cinnamic aldehyde, alpha-amylcinnamic aldehyde, 2-pentyl-3-penyl-2-propenal, or alpha-hexylcinnamic aldehyde; or any combination thereof. In particular, a mixture of two or more of the above aldehydes can be used.

In an example, the aldehyde can be used in conjunction with the above-identified organic esters. In another example, the aldehyde can be used in conjunction with propanoate or acetate organic esters. For example, the propanoate or acetate organic esters can be used in an amount described above in relation to the organic ester. The aldehyde, whether used in conjunction with an organic ester described above, the propanoate or acetate organic esters, or alone, can be used in an amount of not greater than 10%, such as not greater than 5 wt %. For example, the aldehyde can be used in an amount of 0.1 wt % to 5 wt %, such as an amount of 0.3 wt % to 3 wt %, or an amount of 1 wt % to 3 wt %.

In a further example, the cleaning solution includes a surfactant, such as in an amount of 0.1 wt % to 35 wt % based on the total weight of the cleaning solution. For example, the surfactant can be present in an amount of 0.1 wt % to 10 wt %, such as an amount of 1 wt % to 10 wt %, an amount of 5 wt % to 10 wt %, or an amount of 6 wt % to 9 wt % based on the total weight of the cleaning solution. Alternatively, the surfactant can be present in an amount of 1 wt % to 4 wt %, such as an amount of 1 wt % to 3 wt % based on the total weight of the cleaning solution. Further, the surfactant can be included in amount relative to the organic ester, such as at a ratio of surfactant to organic ester in a range of 1:1 to 5:1, such as a range of 2:1 to 5:1, or even a range of 3:1 to 4:1.

In an example, the surfactant includes alpha olefin sulfonate (AOS), aliphatic ether sulfates (AES), alcohol sulfates (AS), linear alkylbenzenesulfonate (LAS), ethoxylated alcohols such as Neodol™ or Tomadol™, phenoxypolyethoxylethanol, such as octyl or nonyl phenoxypolyethoxylethanol (Tergitol™), alkyl ether phosphonate (e.g., Surfonic®), natural surfactants, or any combination thereof. In an example, the surfactant is a nonionic surfactant, an anionic surfactant, a polymeric surfactant, or a cationic surfactant. In particular, the surfactant can be a nonionic surfactant. An exemplary nonionic surfactant includes ethylene oxide or propylene oxide derivatives, such as an ethoxylate ether surfactant. In a particular example, the surfactant includes phenoxypolyethoxylethanol, such as octyl or nonyl phenoxypolyethoxylethanol. In another example, the surfactant is an anionic surfactant. An exemplary anionic surfactant includes a sulfate or sultanate surfactant. In a further example, the surfactant can be a cationic surfactant. Some cationic surfactants are effective at eliminating coliform bacteria.

In a further example, the cleaning solution includes ethylene glycol ether, for example, in an amount of 0.1 wt % to 11 wt % based on the total weight of the cleaning solution. In particular, the cleaning solution can include the ethylene glycol ether in an amount of 0.5 wt % to 7 wt %, such as in an amount of 1.5 wt % to 5 wt %, or an amount of 1 wt % to 3 wt % based on the total weight of the cleaning solution. The ethylene glycol ether does not include ethers of polyethylene glycols having more than two ethylene glycol units. For example, the ethylene glycol ether can have a single ethylene glycol unit. In a particular example, the ethylene glycol ether has a number of carbons in a range of 3 to 10, such as a range of 4 to 8, or a range of 4 to 6 carbons. An exemplary glycol ether includes ethylene glycol methyl ether, ethylene glycol ethyl ether, ethylene glycol butyl ether, ethylene glycol hexyl ether, or any combination thereof. Exemplary ethylene glycol ethers are commonly referred to as Cellosolve™.

The cleaning solution can also include a polymer. In an example, the polymer can be polyethylene glycol, polypropylene glycol, polyvinyl chloride, polyvinyl acetate, partially-hydrolyzed, polyvinyl acetate, ethylene vinyl acetate copolymer, polyvinyl alcohol, polyester such as polyethylene terephthalate (PET), polycarbonate, polyacrylate, acrylic esters, polyacrylonitrile, hydrolyzed polyacrylonitrile, polyolefin such as polyethylene, polypropylene, fluoropolymer or blends or copolymers thereof, polyamide such as Nylon, polysiloxanes, polyurethane, a product of polyethylene diamine and adipic acid, or blends or copolymers thereof, or any combination thereof. For example, the polymer can be an acrylic polymer. In another example, the polymer is polyvinyl acetate. In a further example, the polymer is a silicone polymer. In a further example, the polymer is polyurethane. In an additional example, the polymer is a polyamide. In another example, the polymer is a polyvinyl chloride. In an additional example, the polymer is a poly alkyl glycol, such as polyethylene glycol or polypropylene glycol. Further, the polymer can be a polyolefin, such as polyethylene or polypropylene. An exemplary fluoropolymer can be formed of a homopolymer, copolymer, terpolymer, or polymer blend formed from a monomer, such as tetrafluoroethylene, hexafluoropropylene, chlorotrifluoroethylene, trifluoroethylene, vinylidene fluoride, vinyl fluoride, perfluoropropyl vinyl ether, perfluoromethyl vinyl ether, or any combination thereof. An exemplary fluoropolymer includes polytetrafluoroethylene (PTFE), a fluorinated ethylene propylene copolymer (FEP), a copolymer of tetrafluoroethylene and perfluoropropyl vinyl ether (perfluoroalkoxy or PEA), a copolymer of tetrafluoroethylene and perfluoromethyl vinyl ether (MFA), a copolymer of ethylene and tetrafluoroethylene (ETFE), a copolymer of ethylene and chlorotrifluoroethylene (ECTFE), polychlorotrifluoroethylene (PCTFE), poly vinylidene fluoride (PVDF), terpolymer including tetrafluoroethylene, hexafluoropropylene, and vinylidenefluoride (THV), or any blend or any alloy thereof.

The polymer can be included in an amount not greater than 5 wt %, such as not greater than 3.5 wt %, not greater than 2.5 wt %, not greater than 2 wt %, or even not greater than 1.5 wt % based on the total weight of the cleaning solution. In particular, the polymer can be included in an amount of at least 0.1 wt %, such as in a range of 0.1 wt % to 5 wt % based on the total weight of the cleaning solution.

In addition, the solution can include a fragrance. The fragrance can be included in an amount of not greater than 5 wt %, such as an amount of not greater than 2 wt %, not greater than 1 wt %, not greater than 0.7 wt %, or even not greater than 0.5 wt %. In a further example, the solution can include a colorant or dye. For example, the solution can include not greater than 3 wt % of a colorant.

The cleaning solution can also include quaternary ammonium salts. An exemplary quaternary ammonium salts includes benzalkonium chloride. The quaternary ammonium salt can be included in amount of not greater than 5 wt %, not greater than 4 wt %, or even not greater than 3 wt % based on the total weight of the cleaning solution.

It has been found that the cleaning solution is particularly good at drawing malodorous compounds, such as nitrogenous compounds, away from a surface and binding to them below the surface of a porous material. For example, such malodors can originate from sources such as cooked-fish, pet urine, garbage, smoked-tobacco residue, bathroom smells, natural alkaloids or other amine sources. While the cleaning solution can include fragrances, the cleaning solution can consist essentially of a mixture of components that in combination draw malodors away from a surface and bind to them away from the surface, such as a combination of an organic acid, a surfactant, an organic ester, and an ethylene glycol ether, and optionally a polymer.

Figure 2:
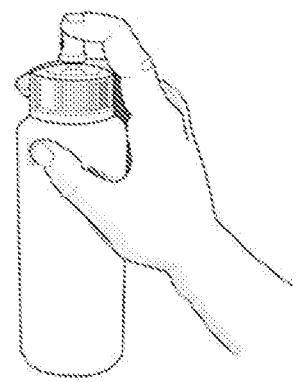
FIG. 2 includes an illustration of an exemplary aerosol spray.

Either or both of the deodorizing solution or the cleaning solutions can be applied as a sprits or aerosol. Alternatively, the deodorizing solution or the cleaning solution can be applied using cloth or sponge. For example, either solution can be included in a spray bottle, as illustrated in FIG. 1, or can be included in a pressurized aerosol can, as illustrated in FIG. 2. The spray bottle illustrated in FIG. 1 is an ambient pressure spray bottle that, when motivated, forces the aqueous solution through a nozzle causing a spray that can be applied to a surface.

In another example, either solution can be included in an aerosol pressurized can as illustrated in FIG. 2. The solution can be maintained under pressure by employing compressed propellant gases such as propane, nitrogen, fluorocarbon, or other gases, or any combination thereof.

The deodorizing solution can be applied to hard surfaces such as natural stone countertops, including granite or marble countertops, Micarta or other vinyl finishes, glass surfaces, or polymeric surfaces. In another example, the deodorizing solution can be applied to drapes, fabrics, carpeting, upholstery, clothes, bedding, or other articles and surfaces. In particular, the deodorizing solution can be applied to surfaces found on the interiors of automobiles. In a further example, the deodorizing solution can be applied to furniture, workbenches, or other hard surfaces. Further, the deodorizing solution can be used in a medical facility, such as a hospital, emergency room, or clinic.

The cleaning solution can also be applied on various surfaces. It has been found that the cleaning solution is particularly beneficial for use with surfaces that are porous as the cleaning solution can trap or bind to malodorous compounds, such as amine compounds, and transport them away from a surface into a porous material. In particular, the cleaning solution is particularly advantageous at treating cloth seats, carpets, overhead materials, and other surfaces within an automobile. Further, it is capable of neutralizing malodorous amines or other nuisance nitrogenous odors (including fish odors, latent tobacco amines and alkaloids). Amine odor sources can include marine-originating food odors, pet odors, odors that arise from slow-release of substance-entrained components in fabrics contaminated, by use of ember-type tobacco products, such as cigarettes or cigars, garbage, trash, bathroom emissions or other nitrogenous sources of odor.

DEODORIZING SOLUTION EXAMPLES

Example 1

Mix titanium dioxide crystal colloid liquid (e.g., from CRISTAL GLOBAL @ Millenium), preferably "S5-300B," at neutral pH with an emulsified polymer. Mix thoroughly and apply to any hard surface, or cloth, fabric, upholstery or other surface. The mixing ratios of ingredients are 2% $TiO_2$ liquid, 9% emulsified polymer (e.g., emulsifiable polymer available from Dow, DuPont, Evonik or others or Minwax, or a latex paint from a supplier such as Kenmore), 1% light alcohol (ethyl or IPA) and 88% water.

Example 2

Mix titanium dioxide crystal colloid liquid (e.g., from CRISTAL GLOBAL @ Millenium), preferably "S5-300B," at neutral pH with an emulsified polymer. Mix thoroughly and apply to any hard surface, or cloth, fabric, upholstery or other surface. The mixing ratios of ingredients are 3% $TiO_2$ colloid liquid, 10% emulsified polymer (see options of Example 1), 1% light alcohol (ethyl or IPA) and 86% water.

Example 3

Mix titanium dioxide crystal colloid liquid (e.g., from CRISTAL GLOBAL @ Millenium), preferably "S5-300B," at pH of 8.0 (adjusted with bicarbonate) with emulsified polymer. Mix thoroughly and apply to any hard surface, or cloth, fabric, upholstery or other surface. The mixing ratios of ingredients are 2% $TiO_2$ colloid liquid, 9% emulsified polymer (see Example 1 options), 1% light alcohol (ethyl or IPA) and 88% water.

Example 4

Add titanium dioxide crystal colloid liquid (e.g., from CRISTAL GLOBAL @ Millenium), preferably "S5-300B," at pH of 9.0 (adjusted with sodium bicarbonate) to emulsified polymer. Mix thoroughly and apply to any hard surface, or cloth, fabric, upholstery or other surface. The mixing ratios of ingredients are 2% $TiO_2$ colloid liquid, 9% emulsified polymer, 1% light alcohol (ethyl or IPA) and 88% water.

Example 5

Mix titanium dioxide crystal colloid liquid (e.g., from CRISTAL GLOBAL @ Millenium), preferably "S5-300B," at pH of 9.5 (adjusted with sodium carbonate) with emulsified polymer. Mix thoroughly and apply to any hard surface, or cloth, fabric, upholstery or other surface. The mixing ratios of ingredients are 2% $TiO_2$ colloid liquid, 9% emulsified polymer, 1% light alcohol (ethyl or IPA) and 88% water.

Example 6

Add titanium dioxide crystal colloid liquid (e.g., from CRISTAL GLOBAL @ Millenium), preferably "S5-300B," which is approximately 18% active at neutral pH to emulsified polymer. Mix thoroughly and apply to any hard surface, or cloth, fabric, upholstery or other surface. The mixing ratios of ingredients are 4% $TiO_2$ colloid liquid, 9% emulsified polymer, 1% light alcohol (ethyl or IPA) and 86% water.

Example 7

Add emulsified polymer to the titanium dioxide crystal colloid liquid (e.g., CRISTAL GLOBAL @ Millenium), preferably "S5-300B," which is approximately 18% active. Do so at neutral pH. Apply mixture to any hard surface, cloth, fabric, upholstery or other surface. The mixing ratios of ingredients are 4% $TiO_2$ colloid liquid, 9% emulsified polymer, 1% light alcohol (ethyl or IPA) and 86% water.

Example 8

Mix titanium dioxide crystal colloid liquid (e.g., CRISTAL GLOBAL @ Millenium), preferably "S5-300B," at neutral pH with emulsified PEG polymer. The mixing ratios of ingredients are 2% TiO$_2$ colloid liquid, 9% emulsified polymer, 1% light alcohol (ethyl or IPA) and 88% water.

Example 9

Mix titanium dioxide crystal colloid liquid (e.g., form CRISTAL GLOBAL @ Millenium), preferably "S5-300B," at neutral pH with emulsified PPG (polypropylene glycol) polymer. The mixing ratios of ingredients are 2% TiO$_2$ colloid liquid, 9% emulsified polymer, 1% light alcohol (ethyl or IPA) and 88% water.

Example 10

Add emulsified polymer, such as polyacrylic emulsion, to 18%-active titanium dioxide colloid liquid (e.g., from CRISTAL GLOBAL @ Millenium, preferably "S5-300B) at a pH of between 7.0 and 8.0. Apply mixture to any surface area. The mixing ratios of ingredients are 3% TiO$_2$ colloid liquid, 10% of the emulsified polyacrylic, 1% light alcohol (ethyl or IPA) and 86% water.

Example 11

Add emulsified polymer, such as polyacrylic emulsion, to 18%-active titanium dioxide colloid liquid (e.g., from CRISTAL GLOBAL @ Millenium—preferably "S5-300B) at a pH of 9.0. Apply mixture to any surface area. The mixing ratios of ingredients are 3% TiO$_2$ colloid liquid, 10% of the emulsified polyacrylic, 1% light alcohol (ethyl or IPA) and 86% water.

Example 12

Mix titanium dioxide crystal colloid liquid (e.g., from CRISTAL GLOBAL @ Millenium), preferably "S5-300B," at neutral pH with emulsified polymer. Mix thoroughly and apply to any hard surface, or cloth, fabric, upholstery or other surface. The mixing ratios of ingredients are 4% TiO$_2$ colloid liquid, 15% emulsified polymer, 1% light alcohol (ethyl or IPA) and 80% water.

Example 13

Mix titanium dioxide crystal colloid liquid (e.g., from CRISTAL GLOBAL @ Millenium), preferably "S5-300B," at neutral pH with emulsified polymer. Mix thoroughly and apply to any hard surface, or cloth, fabric, upholstery or other surface. The mixing ratios of ingredients are 6% TiO$_2$ colloid liquid, 8% emulsified polymer, 4% light alcohol (ethyl or IPA) and 82% water.

Example 14

Mix titanium dioxide crystal colloid liquid (e.g., from CRISTAL GLOBAL @ Millenium), preferably "S5-300B," at pH of 12.0 with emulsified PPG (polypropylene glycol) polymer. The mixing ratios of ingredients are 2% TiO$_2$ colloid liquid, 9% emulsified polymer, 1% light alcohol (ethyl or IPA) and 88% water.

Example 15

Mix titanium dioxide crystal colloid liquid (e.g., from CRISTAL GLOBAL @ Millenium), preferably "S5-300B," at pH of 12.0 with emulsified polymer. Mix thoroughly and apply to any hard surface, or cloth, fabric, upholstery or other surface. The mixing ratios of ingredients are 2% TiO$_2$ colloid liquid, 9% emulsified polymer, 1% light alcohol (ethyl or IPA) and 88% water.

Example 16

Mix titanium dioxide crystal colloid liquid (e.g., CRISTAL GLOBAL @ Millenium), preferably "S5-300B," at neutral pH with emulsified polymer. Mix thoroughly and apply to any hard surface, or cloth, fabric, upholstery or other surface. The mixing ratios of ingredients are 6% TiO$_2$ colloid liquid, 12% emulsified polymer, 4% light alcohol (ethyl or IPA) and 78% water.

Example 17

Mix titanium dioxide crystal colloid liquid (e.g., from CRISTAL GLOBAL @ Millenium), preferably "S5-300B," at neutral pH with emulsified polymer. Mix thoroughly and apply to any hard surface, or cloth, fabric, upholstery or other surface. The mixing ratios of ingredients are 6% TiO$_2$ colloid liquid, 14% emulsified polymer, 5% light alcohol (ethyl or IPA) and 75% water.

Example 18

Add emulsified polymer, such as PEG emulsion, to 18%-active titanium dioxide colloid liquid (e.g., from CRISTAL GLOBAL @ Millenium—preferably "S5-300B) at a pH of between 7.0 and 8.0. Apply mixture to any surface area. The mixing ratios of ingredients are 3% TiO$_2$ colloid liquid as detailed above, 10% of the emulsified PEG, 1% light alcohol (ethyl or IPA) and 86% water.

Example 19

Add emulsified polymer, such as PPG (polypropylene glycol) polyacrylic copolymer emulsion, to 18%-active titanium dioxide colloid liquid a neutral pH. Apply mixture to any surface area. The mixing ratios of ingredients are 3% TiO$_2$ colloid liquid as detailed above, 10% of the emulsified polyacrylic, 1% light alcohol (ethyl or IPA) and 86% water.

Example 20

Mix titanium dioxide crystal colloid liquid (e.g., CRISTAL GLOBAL @ Millenium), preferably "S5-300B," at a pH of 9.5 with emulsified polymer. Mixing ratios of ingredients are 4% TiO$_2$ colloid liquid, 15% emulsified polymer, 1% light alcohol (ethyl or IPA) and 80% water.

Example 21

Mix titanium dioxide crystal colloid liquid (e.g., CRISTAL GLOBAL @ Millenium), preferably "S5-300B," at pH 10.0 with emulsified latex polyamide. The mixing ratios of ingredients are 6% TiO$_2$ colloid liquid, 8% emulsified polymer, 4% light alcohol (ethyl or IPA) and 82% water.

Example 22

Mix titanium dioxide crystal colloid liquid (e.g., CRISTAL GLOBAL @ Millenium), preferably "S5-300B," at pH of 12.0 with emulsified polyamide. The mixing ratios of ingredients are 2% TiO$_2$ colloid liquid, 9% emulsified polyamide, 1% IPA (isopropyl alcohol) and 88% water.

Example 23

Add emulsified polymer, such as PVA (partially hydrolyzed polyvinyl acetate) emulsion, to 18%-active titanium dioxide colloid liquid (e.g., from CRISTAL GLOBAL @ Millenium preferably "S5-300B") at a pH of between 7.0 and 8.0. Apply mixture to any surface area. The mixing ratios of ingredients are 3% $TiO_2$ colloid liquid, 10% of the emulsified PVA, 1% light alcohol (ethyl or IPA) and 86% water.

Example 24

Figure 3:
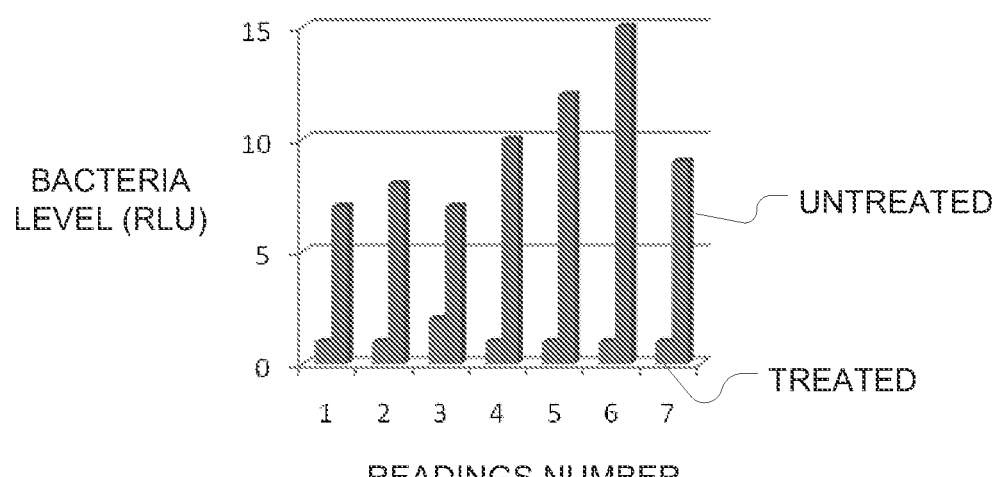
FIG. 3, FIG. 4, and FIG. 5 include graph illustrations of deodorizer performance.
Figure 4:
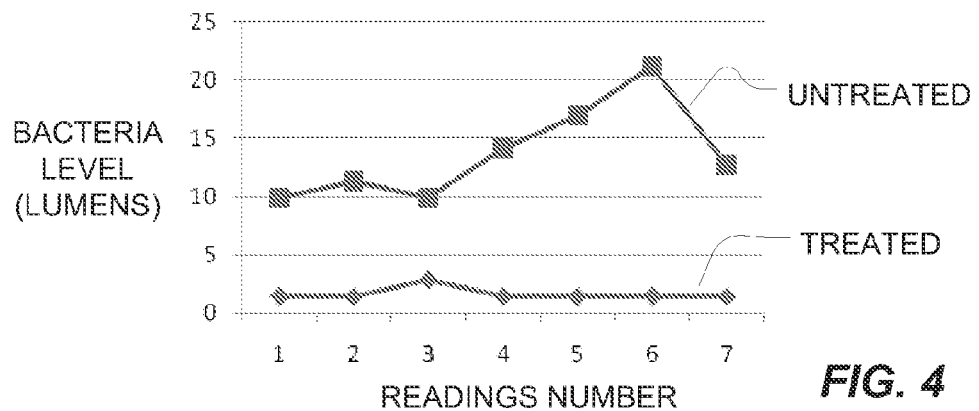

The deodorizing solution of Example 10 is applied to surfaces and tested for activity against bacterial growth. After 17 minutes under uniform artificial light (254 nm), the bacteria levels are measured in relative light units (RLUs). As illustrated in FIG. 3, the treated surfaces exhibit significantly lower bacterial activity. Similar results are seen when measured in lumens, as illustrated in FIG. 4.

Figure 5:
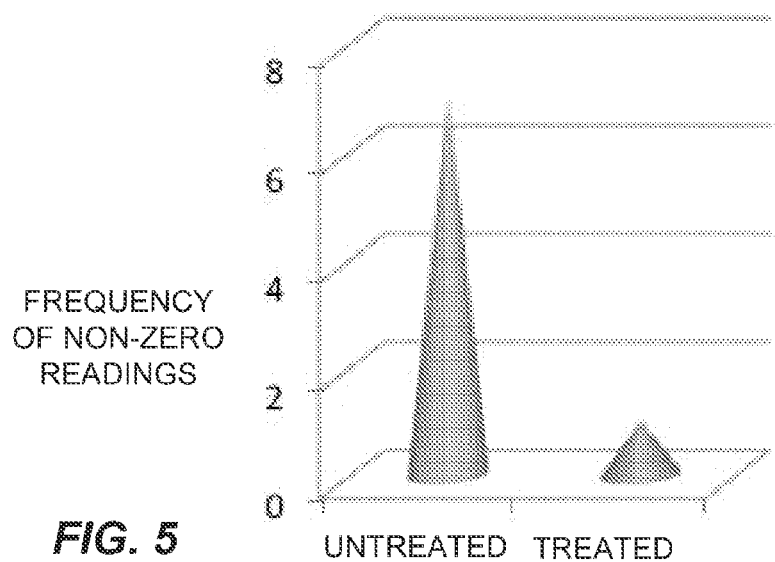

Elimination of bacteria is measured based on the presence of adenosine triphosphate (ATP). As illustrated in FIG. 5, the number of bacterial colonies is significantly fewer when treated with the deodorizing solution.

CLEANING SOLUTION EXAMPLES

Example 1

An aqueous mix of ethyl butyrate and Tergitol® in effective emulsifying proportions (between 3:1 and 4:1 Tergitol®:ethyl butyrate) with a quaternary ammonium salt and a fragrance is formed.

Example 2

An aqueous mix of methyl salicylate and Tergitol® in effective emulsifying proportions (between 3:1 and 4:1 Tergitol®:methyl salicylate) with a quaternary ammonium salt and a fragrance is formed.

Example 3

A mixture of ethyl butyrate, or methyl butyrate, and C-550 in effective emulsifying proportions (between 3:1 and 4:1 C-550:ethyl butyrate) is prepared. A second solution is prepared to also include a quaternary ammonium salt and a fragrance.

Example 4

The aqueous mix of methyl butyrate and alcohol sulfate in effective emulsifying proportions (between 3:1 and 4:1 alcohol sulfate:methyl butyrate) is prepared.

Example 5

An aqueous mix of ethyl valerate and methyl ester sulfonate in effective emulsifying proportions (between 3:1 and 4:1 methyl ester sulfonate:ethyl valerate) is prepared. A second solution is prepared to also include a quaternary ammonium salt or a fragrance.

Example 6

An aqueous mix of methyl butyrate and Tergitol® in effective emulsifying proportions (between 3:1 and 4:1 Tergitol®:methyl butyrate) is prepared. A second solution is prepared to additionally include a quaternary ammonium salt ingredient and a fragrance.

Example 7

An aqueous mix of methyl butyrate and alcohol sulfate in effective emulsifying proportions (between 3:1 and 4:1 alcohol sulfate:methyl butyrate) is prepared.

Example 8

An aqueous mix of ethyl amylate and succinate surfactant (between 3:1 and 4:1 succinate surfactant:ethyl amylate) is prepared.

Example 9

An aqueous mix of an organic ester and a surfactant selected from AOS, AS AES, LAS, NEODOL, SURFONIC, TERGITOL or NATURALS is prepared. A second solution is prepared to additionally include a quaternary ammonium salt ingredient or a fragrance.

Example 10

A solution is prepared that includes the mixture of Example 9 and propionate and acetate derivatives.

Example 11

An aqueous mix of methyl butyrate and alcohol sulfate in effective emulsifying proportions (between 3:1 and 4:1 alcohol:methyl butyrate) is prepared.

Example 12

Propionate and acetate derivatives are mixed with methyl butyrate and Tomadol™ in effective emulsifying proportions. A second solution is prepared to also include a quaternary ammonium salt ingredient or a fragrance.

Example 13

A mixture of ethyl butyrate, or methyl butyrate, and C-550 in effective emulsifying proportions (between 3:1 and 4:1 C-550:methyl/ethyl butyrate) is prepared. As second solution is prepared to also include a quaternary ammonium salt ingredient or a fragrance.

Example 14

An aqueous mix of ethyl amylate and MES (between 3:1 and 4:1 MES:ethyl amylate) is prepared. A second solution is prepared to also include a quaternary ammonium salt or a fragrance.

Example 15

A water mix of methyl salicylate, or similar ester, and surfactant is prepared.

Example 16

An aqueous mix of butyrate or hexanoate esters with alcohol sulfate in effective emulsifying proportions (between 3:1 and 4:1 alcohol sulfate:butyrate or hexanoate) is prepared.

Example 17

A mixture including hexanoate and propionate and acetate derivatives are prepared.

Example 18

An aqueous mix of AES or AS and low-molecular weight organic acid esters is prepared.

Example 9

An aqueous mix of esters and a cationic surfactant in effective emulsifying proportions (between 3:1 and 4:1 cationic surfactant:organic ester), a quaternary ammonium salt ingredient and a fragrance is prepared.

Example 20

A mixture of an organic ester, a surfactant and a colorant is prepared.

Example 21

A solution is prepared to include the solution of Example 1 and a Cellosolve ether.

Example 22

A solution is prepared to include the solution of Example 2 and a Cellosolve ether.

Example 23

A solution is prepared to include the solution of Example 3 and a Cellosolve ether.

Example 24

A solution is prepared to include the solution of Example 4 and a Cellosolve ether.

Example 25

A solution is prepared to include the solution of Example 5 and a Cellosolve ether.

Example 26

A solution is prepared to include the solution of Example 6 and a Cellosolve ether.

Example 27 solution is prepared that includes an aqueous base, 5 wt % citric acid, 3 wt % ethyl butyrate, 9 wt % Tergitol, 3 wt % Cellosolve, 03 wt % fragrance, 0.75 wt % of an acrylate polymer, and 0.4 wt % dye.

Example 28

A solution is prepared that includes an aqueous base, 5 wt % citric acid, 3 wt % ethyl acetate, 3 wt % aldehyde (n combination of dodecanal and citral), 9 wt % Tergitol, 3 wt % Cellosolve, 0.3 wt % fragrance, 0.75 wt % of an acrylate polymer, and 0.4 wt % dye.

Example 29

A solution is prepared that includes an aqueous base, 5 wt % citric acid, 3 wt % ethyl butyrate, 3 wt % aldehyde (decanal and citral), 9 wt % Tergitol, 3 wt % Cellosolve, 0.3 wt % fragrance, 0.75 wt % of an acrylate polymer, and 0.4 wt % dye.

In a first embodiment, a cleaning solution includes an aqueous base, 0.1 wt % to 10 wt % of an organic acid, 0.1 wt % to 35 wt % of a surfactant, 0.1 wt % to 10 wt % of an organic ester derived from a carboxylic acid having at least 4 carbons, and 0.1 wt % to 1 wt % of an ethylene glycol ether.

In an example of the first embodiment, the organic acid is included in an amount of 0.1 wt % to 10 wt %. In another example, the organic acid includes ascorbic acid, aspartic acid, citric acid, maleic acid, oxalic acid, succinic acid, glycolic acid, lactic acid, malic acid, tartaric acid, glutaric acid, mandelic acid, malonic acid, adipic acid, phthalic acid, or any combination thereof. In particular, the organic acid is citric acid.

In an additional example of the first embodiment, the surfactant is included in an amount of 1 wt % to 10 wt %. In a further example of the first embodiment, the surfactant is a nonionic surfactant, such as an ethoxylate surfactant. In another example of the first embodiment, the surfactant is an anionic surfactant, such as a sulfate or sulfonate surfactant.

In a further example of the first embodiment, the carboxylic acid includes 4 to 16 carbons. For example, the carboxylic acid can include to 10 carbons, such as 4 to 8 carbons. In another example, the organic ester is a methyl or ethyl ester of the carboxylic acid. For example, the carboxylic acid can be aliphatic. In another example, the carboxylic acid is aromatic.

In another example of the first embodiment, the ethylene glycol ether has 3 to 10 carbons. For example, the ethylene glycol ether has 4 to 8 carbons, such as 4 to 6 carbons.

In an additional example, of the first embodiment, the cleaning solution includes not greater than 1.0 wt % of a fragrance. In another example, the cleaning solution further includes not greater than 5 wt % of a polymer. In a further example the cleaning solution includes not greater than 3 wt % of a colorant. In another example, the cleaning solution further includes not greater than 10 wt % of an aldehyde.

In a second embodiment, a cleaning solution consists essential of an aqueous base, 0.1 wt % to 10 wt % of an organic acid, 0.1 wt % to 10 wt % of a surfactant, 0.1 wt % to 10 wt % of an organic ester derived from a carboxylic acid having at least 4 carbons, 0.1 wt % to 11 wt % of an ethylene glycol ether, and not greater than 5 wt % of a polymer.

In an example of the second embodiment, the organic acid includes ascorbic acid, aspartic acid, citric acid, maleic acid, oxalic acid, succinic acid, glycolic acid, lactic acid, malic acid, tartaric acid, glutaric acid, mandelic acid, malonic acid, adipic acid, phthalic acid, or any combination thereof.

In another example of the second embodiment, the surfactant is a nonionic surfactant, such as an ethoxylate surfactant. In an additional example, the surfactant is an anionic surfactant.

In a further example, the carboxylic acid includes 4 to 16 carbons. In an additional example, the organic ester is a methyl or ethyl ester of the carboxylic acid. In another example, the carboxylic acid is aliphatic. In a further example, the carboxylic acid is aromatic.

In an additional example, the ethylene glycol ether has 3 to 10 carbons.

In a third embodiment, a cleaning solution consists essential of an aqueous base, 0.1 wt % to 10 wt % of an organic acid, 0.1 wt % to 10 wt % of a surfactant, 0.1 wt % to 10 wt % of an organic ester, not greater than 10 wt % of an aldehyde, 0.1 wt % to 11 wt % of an ethylene glycol ether, and not greater than 5 wt % of a polymer.

In an example of the third embodiment, the organic acid includes ascorbic acid, aspartic acid, citric acid, maleic acid, oxalic acid, succinic acid, glycolic acid, lactic acid, malic acid, tartaric acid, glutaric acid, mandelic acid, malonic acid, adipic acid, phthalic acid, or any combination thereof.

In another example, the surfactant is a nonionic surfactant, such as an ethoxylate surfactant. In an additional example, the surfactant is an anionic surfactant.

In an additional example of the third embodiment, the organic ester is formed of a carboxylic acid including 4 to 16 carbons. In another example, the organic ester is a methyl or ethyl ester of the carboxylic acid. In a particular example, the carboxylic acid is aliphatic. In a further example, the carboxylic acid is aromatic.

In an example of the third embodiment, the ethylene glycol ether has 3 to 10 carbons.

In a fourth embodiment, a cleaning solution consists of an aqueous base, 0.1 wt % to 10 wt % of an organic acid, not greater than 5.0 wt % of a fragrance, 0.1 wt % to 35 wt % of a surfactant, 0.1 wt % to 10 wt % of an organic ester derived from a carboxylic acid having at least 4 carbons, not greater than 10 wt % of an aldehyde, 0.1 wt % to 11 wt % of an ethylene glycol ether, not greater than 5 wt % of a water dispersible polymer, and not greater than 3 wt % colorant.

In an example of the fourth embodiment, the organic acid is included in an amount of 0.1 wt % to 8 wt %. The organic acid can include ascorbic acid, aspartic acid, citric acid, maleic acid, oxalic acid, succinic acid, glycolic acid, lactic acid, malic acid, tartaric acid, glutaric acid, mandelic acid, malonic acid, adipic acid, phthalic acid, or any combination thereof. In a particular example, the organic acid is citric acid.

In another example of the fourth embodiment, the surfactant is included in an amount of 1 wt % to 10 wt %. In a particular example, the surfactant is a nonionic surfactant, such as an ethoxylate surfactant. In another example, the surfactant is an anionic surfactant, such as a sulfate or sulfonate surfactant.

In an additional example of the fourth embodiment, the carboxylic acid includes 4 to 16 carbons. For example, the carboxylic acid can include 4 to 10 carbons, such as 4 to 8 carbons. In a particular example, the organic ester is a methyl or ethyl ester of the carboxylic acid. In an example, the carboxylic acid is aliphatic. In another example, the carboxylic acid is aromatic.

In a further example of the fourth embodiment, the ethylene glycol ether has 3 to 10 carbons. For example, the ethylene glycol ether has 4 to 8 carbons, such as 4 to 6 carbons.

In a fifth embodiment, a deodorizing solution includes an aqueous base, 0.1 wt % to 6 wt % titanium dioxide having an average particle size of not greater than 100 nm, 0.5 wt % to 5 wt % alcohol, and 3 wt % to 15 wt % of a polymer.

In an example of the fifth embodiment, the average particle size is not greater than 60 nm. In another example, the average particle size can be at least 3 nm.

In a further example of the fifth embodiment, the deodorizing solution further includes 0.3 wt % to 5 wt % of a surfactant.

In an additional example of the fifth embodiment, the titanium dioxide is included, in an amount of 1 wt % to 6 wt %.

In another example of the fifth embodiment, the alcohol includes isopropyl alcohol. In a particular example, the polymer includes acrylic. Further, the polymer can be included in an amount in a range of 8 wt % to 15 wt %.

Note that not all of the activities described above in the general description or the examples are required, that a portion of a specific activity may not be required, and that one or more further activities may be performed in addition to those described. Still further, the orders in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A cleaning solution consisting of:
   an aqueous base;
   0.1 wt % to 10 wt % of an organic acid;
   0.1 wt % to 35 wt % of a nonionic surfactant;
   0.1 wt % to 10 wt % of an organic ester derived from a carboxylic acid having at least 4 carbons;
   0.1 wt % to 11 wt % of an ethylene glycol ether;
   not greater than 1.0 wt % of a fragrance;
   not greater than 10 wt % of an aldehyde; and
   an acrylic polymer in an amount of not greater than 1.5 wt %.

2. The cleaning solution of claim 1, wherein the organic acid is included in an amount of 0.5 wt % to 7 wt %.

3. The cleaning solution of claim 1, wherein the organic acid includes ascorbic acid, aspartic acid, citric acid, maleic acid, oxalic acid, succinic acid, glycolic acid, lactic acid, malic acid, tartaric acid, glutaric acid, mandelic acid, malonic acid, adipic acid, phthalic acid, or any combination thereof.

4. The cleaning solution of claim 3, wherein the organic acid is citric acid.

5. The cleaning solution of claim 1, wherein the nonionic surfactant includes an ethoxylate surfactant.

6. The cleaning solution of claim 1, wherein the carboxylic acid includes 4 to 16 carbons.

7. The cleaning solution of claim 1, wherein the organic ester is a methyl or ethyl ester of the carboxylic acid.

8. The cleaning solution of claim 1, wherein the carboxylic acid is aliphatic.

9. The cleaning solution of claim 1, wherein the carboxylic acid is aromatic.

10. The cleaning solution of claim 1, wherein the ethylene glycol ether has 3 to 10 carbons.

11. The cleaning solution of claim 1, further comprising not greater than 3 wt % of a colorant.

12. A cleaning solution consisting of:
an aqueous base;
0.1 wt % to 10 wt % of an organic acid;
0.1 wt % to 10 wt % of a surfactant;
0.1 wt % to 10 wt % of an organic ester derived from a carboxylic acid having at least 4 carbons;
0.1 wt % to 11 wt % of an ethylene glycol ether; and
an acrylic polymer in an amount of not greater than 1.5 wt %.

13. The cleaning solution of claim 12, wherein the surfactant is a nonionic surfactant.

14. A cleaning solution consisting of:
an aqueous base;
0.1 wt % to 10 wt % of an organic acid including ascorbic acid, aspartic acid, citric acid, maleic acid, oxalic acid, succinic acid, glycolic acid, lactic acid, malic acid, tartaric acid, glutaric acid, mandelic acid, malonic acid, adipic acid, phthalic acid, or any combination thereof;
0.1 wt % to 10 wt % of a phenoxypolyethoxylethanol surfactant;
0.1 wt % to 10 wt % of an organic ester derived from a carboxylic acid having 4 to 8 carbons;
not greater than 10 wt % of an alkyl-aldehyde;
0.1 wt % to 11 wt % of an ethylene glycol ether excluding ethers of polyethylene glycol having more than two ethylene glycol units; and
an acrylic polymer in an amount of not greater than 1.5 wt %.

15. The cleaning solution of claim 1, wherein the nonionic surfactant includes phenoxypolyethoxylethanol.

16. The cleaning solution of claim 6, wherein the carboxylic acid includes 4 to 8 carbons.

17. The cleaning solution of claim 10, wherein the ethylene glycol ether has 4 to 6 carbons.

18. The cleaning solution of claim 12, wherein the surfactant includes phenoxypolyethoxylethanol.

19. The cleaning solution of claim 12, wherein the organic acid includes citric acid.

20. The cleaning solution of claim 12, wherein the carboxylic acid has 4 to 8 carbons.

* * * * *